(12) United States Patent
     Wang

(10) Patent No.: US 12,016,668 B2
(45) Date of Patent: Jun. 25, 2024

(54) MAGNETIC INDUCTION MOLECULAR IMAGING METHOD AND MAGNETIC INDUCTION MOLECULAR IMAGING SYSTEM FOR BIOLOGICAL TISSUE DETECTION

(71) Applicant: Shenzhen Technology University, Guangdong (CN)

(72) Inventor: Lulu Wang, Guangdong (CN)

(73) Assignee: SHENZHEN TECHNOLOGY UNIVERSITY, Shenzhen (CN)

( * ) Notice: Subject to any disclaimer, the term of this patent is extended or adjusted under 35 U.S.C. 154(b) by 770 days.

(21) Appl. No.: 17/043,823

(22) PCT Filed: Dec. 2, 2019

(86) PCT No.: PCT/CN2019/122388
     § 371 (c)(1),
     (2) Date: Sep. 30, 2020

(87) PCT Pub. No.: WO2021/077547
     PCT Pub. Date: Apr. 29, 2021

(65) Prior Publication Data
     US 2023/0108098 A1    Apr. 6, 2023

(30) Foreign Application Priority Data
     Oct. 25, 2019   (CN) .......................... 201911022541.3

(51) Int. Cl.
     *A61B 5/0522*   (2021.01)
     *A61B 5/00*     (2006.01)
     *G01R 33/12*    (2006.01)

(52) U.S. Cl.
     CPC ............ *A61B 5/0522* (2013.01); *A61B 5/704* (2013.01); *G01R 33/1276* (2013.01)

(58) Field of Classification Search
     CPC ..... A61B 5/0522; A61B 5/704; A61B 5/0033; G01R 33/1276; G01R 33/0094
     See application file for complete search history.

(56) References Cited

U.S. PATENT DOCUMENTS

| 9,395,425 B2 * | 7/2016 | Diamond | ............... A61B 5/245 |
| 2011/0221438 A1 * | 9/2011 | Goodwill | ............. A61B 5/0515 |
| | | | 324/301 |

FOREIGN PATENT DOCUMENTS

| CN | 10747039 | * 12/2017 | .......... A61M 31/002 |

* cited by examiner

*Primary Examiner* — Peter Luong
(74) *Attorney, Agent, or Firm* — Michael Ye; Rimon Law

(57) ABSTRACT

A magnetic induction molecular imaging method and a magnetic induction molecular imaging system for biological tissue detection, comprises a detection bed, a magnetic nanoparticle device, a magnetic field generating device, a signal receiving and transmitting device, a magnetic field signal acquisition device and computer equipment, wherein the magnetic nanoparticle device is used for sending magnetic nanoparticles to a to-be-detected area of the detection bed; the magnetic field generating device is used for generating and transmitting electromagnetic waves to the signal receiving and transmitting device; the signal receiving and transmitting device is used for receiving the electromagnetic waves transmitted by the magnetic field generating device; the magnetic field signal acquisition device is used for acquiring scattered electric field information and scattered magnetic field information, based on the magnetic nanoparticles, of the to-be-detected area detected by each sensor on sensor arrays.

10 Claims, 12 Drawing Sheets

MAGNETIC INDUCTION MOLECULAR IMAGING METHOD AND MAGNETIC INDUCTION MOLECULAR IMAGING SYSTEM FOR BIOLOGICAL TISSUE DETECTION

CROSS REFERENCE TO RELATED APPLICATION

This application is for entry into the U.S. National Phase under § 371 for International Application No. PCT/CN2019/122388 having an international filing date of Dec. 2, 2019, and from which priority is claimed under all applicable sections of Title 35 of the United States Code including, but not limited to, Sections 120, 363, and 365(c) and which in turn claims priority under 35 USC 119 to Chinese Patent Application No. 201911022541.3 filed on Oct. 25, 2019.

TECHNICAL FIELD

The disclosure belongs to the technical field of magnetic induction imaging and specifically relates to a magnetic induction molecular imaging method and a magnetic induction molecular imaging system for biological tissue detection.

BACKGROUND

Magnetic induction imaging is a novel medical imaging method and provides the possibility for early diagnosis of brain diseases. Along with the application and popularization of the magnetic induction imaging technology in the field of biological images, the requirements of people for high-definition microwave images and rapid imaging are growing increasingly. However, due to the defects of algorithm and imaging system design, magnetic induction imaging still has many defects, such as low image resolution, long imaging time, high calculation cost, low sensitivity to small tumors and the like.

SUMMARY

In order to at least overcome the problems of low image resolution, long imaging time, high calculation cost, low sensitivity to small tumors, and the like in the related magnetic induction imaging technology to a certain extent, the embodiment of the disclosure provides a magnetic induction molecular imaging method and a magnetic induction molecular imaging system for biological tissue detection. Details are as follows:

On one hand, the magnetic induction molecular imaging system for biological tissue detection comprises a detection bed, a magnetic nanoparticle device, a magnetic field generating device, a signal receiving and transmitting device, a magnetic field signal acquisition device, and computer equipment;
  the detection bed is used for bearing the weight of a to-be-detected organism;
  the magnetic nanoparticle device comprises a slow-release device, the slow release device is filled with magnetic nanoparticles, and when the to-be-detected organism is measured, the slow release device sends the magnetic nanoparticles to a to-be-detected area of the detection bed;
  the magnetic field generating device comprises an electromagnetic wave generating module and Helmholtz coil modules, the electromagnetic wave generating module is used for generating and transmitting electromagnetic waves to the signal receiving and transmitting device, and the Helmholtz coil modules are used for generating an excitation magnetic field for the to-be-detected area;
  the signal receiving and transmitting device comprises a scanner comprising N sensor arrays, N is a natural number, the distance from the sensor arrays to a to-be-detected organ is far larger than one working wavelength, and sensors are used for receiving the electromagnetic waves transmitted by the magnetic field generating device;
  the magnetic field signal acquisition device comprises a data acquisition card, and the data acquisition card is used for acquiring scattered electric field information and scattered magnetic field information, based on the magnetic nanoparticles, of the to-be-detected area detected by each sensor on the sensor arrays and sending the scattered electric field information and the scattered magnetic field information to the computer equipment;
  the computer equipment is used for analyzing the internal tissue structure state of the to-be-detected organ according to the scattered electric field information and the scattered magnetic field information to form an image.

Further optionally, the slow release device is a fiber tube, the upper end and the lower end of the fiber tube are fixed through a support positioning device, and the support positioning device comprises a positioning shell fixedly connected with the end of the fiber tube.

Further optionally, the number of the Helmholtz coil modules is two, and the two Helmholtz coil modules are respectively arranged at two ends of the sensor arrays.

Further optionally, the sensor arrays are implemented by columnar sensor arrays, and all sensors are uniformly distributed in a circular ring shape around a target area by taking the axis of the detection bed as the center and are positioned at the same height.

Further optionally, the magnetic nanoparticles are ferroferric oxide.

On the other hand, the magnetic induction molecular imaging method for biological tissue detection realized based on the system comprises the following steps:
  S1, enabling the to-be-detected organism to lie on the detection bed, and exposing the to-be-detected organ in the to-be-detected area;
  S2, sending quantitative magnetic nanoparticles to the to-be-detected area according to preset settings by the magnetic nanoparticle device;
  S3, emitting uninterrupted time-harmonic electromagnetic wave signals with a specific frequency and transmitting the signals to the sensor arrays of the signal receiving and transmitting device by the magnetic field generating device, and adjusting the scanning positions of the Helmholtz coils so that the Helmholtz coils generate the excitation magnetic field for the to-be-detected area of the detection bed;
  S4, detecting the time-harmonic electromagnetic wave signals of the to-be-detected area of the detection bed by the sensor arrays of the signal receiving and transmitting device;
  S5, acquiring the scattered electric field information and the scattered magnetic field information, based on the magnetic nanoparticles, of the to-be-detected area detected by each sensor on the sensor arrays through the data acquisition card by the magnetic field signal acquisition device; and S6, analyzing the internal tissue structure state of the to-be-detected organ according to the scattered electric field information and the scattered magnetic field information by the computer equipment to form the image.

Further optionally, the step of analyzing the internal tissue structure state of the to-be-detected organ according to the scattered electric field information and the scattered magnetic field information by the computer to form the image comprises the step of constructing a two-dimensional image of a target object through an inverse Fourier transform processing mode based on the amplitude and the phase of the dielectric property and the conductivity distribution of biological tissue and the magnetic susceptibility intensity information of the internal tissue by the computer.

Further optionally, the step of constructing the two-dimensional image of the target object through the inverse Fourier transform processing mode based on the amplitude and the phase of the dielectric property and the conductivity distribution of the biological tissue and the magnetic susceptibility intensity information of the internal tissue by the computer comprises the step of carrying out two-dimensional inverse Fourier transform on visibility function signals acquired by any two sensors to obtain a two-dimensional reconstructed image of the target object.

Further optionally, the acquisition process of a visibility function comprises the following steps:

extracting scattered magnetic field information of the magnetic nanoparticles in the to-be-detected area containing the magnetic nanoparticles detected by any two sensors; and comparing differences of the scattered magnetic field information detected by the two sensors to obtain the visibility function of the two sensors.

Further optionally, the acquisition process of the visibility function further comprises the following steps:

extracting the magnetization information and the scattered electric field information, detected by all the sensors, of the magnetic nanoparticles in the to-be-detected area; and comparing information differences detected by any two sensors one by one to obtain the sum of visibility functions, including phase delay and/or amplitude difference information, namely a total visibility function.

According to the magnetic induction molecular imaging method and the magnetic induction molecular imaging system for biological tissue detection provided by the embodiment of the disclosure, organism detection is carried out by utilizing the imaging property of the magnetic nanoparticles and the dielectric property of the biological tissue, and the basic principle is as follows: according to different magnetic susceptibilities of various different magnetic nanoparticles, strain is different after an external magnetic field or alternating vibration is applied, the change of magnetic susceptibility is different mainly, and scattered magnetic fields of target biological tissues are different under the irradiation of the electromagnetic waves according to different dielectric properties and conductivities of different biological tissues, so that the appearance image of the target or the structural imaging in the medium target can be reconstructed by analyzing and processing the morphological change and the scattered magnetic fields, the spatial magnetic field distribution can also be visually displayed, compared with fusion imaging, the imaging speed is higher, the imaging quality is better, and the method and the system can be used for the fields of biomedical imaging, disease diagnosis, foreign matter detection and the like.

It should be understood that the above general description and later detail description are just exemplary and explanatory, but cannot restrict the disclosure.

BRIEF DESCRIPTION OF THE DRAWINGS

The accompanying diagrams herein are merged into the specification and constitute a part of the specification, illustrate the embodiment according to the disclosure, and are used for explaining the principle of the disclosure together with the specification.

DESCRIPTION OF THE EMBODIMENTS

The exemplary embodiment is illustrated in detail herein, and typical examples are illustrated in accompanying diagrams. When the following description refers to the accompanying diagrams, except as otherwise noted, the same figures in different accompanying diagrams show the same or similar elements. The enforcement modes described in the following exemplary embodiments do not represent all enforcement modes, which are the same as the disclosure. Oppositely, those are examples of devices and methods which are expatiatory in the claims and are the same in some aspects of the disclosure.

Due to the unique performance, the magnetic nanoparticles have wide application values and particularly bring new opportunities and hopes to the treatment of human diseases in the fields of biological separation, clinical diagnosis, tumor treatment, targeted transportation, and tissue engineering. In recent years, magnetic nanoparticles can be used as a contrast agent for magnetic resonance imaging and can be used as a thermotherapy medium for cancer thermotherapy, so that the magnetic nanoparticles can be applied to magnetic tissue engineering to attract extensive attention of researchers.

Molecular imaging is a technology for quantitatively measuring physiological changes in an organism by using probes or signals and can develop specific molecular and cellular targets into sources of image contrast, and the medical imaging technology is an important tool in biomedical and treatment diagnosis research. In recent years, due to the application of nanotechnology, molecular imaging technology is developed rapidly. By using nanotechnology, imaging tools and labeled molecules are greatly improved to achieve the effects of early diagnosis and monitoring treatment of diseases.

In the research process of the magnetic induction imaging technology, the applicant accidentally finds that if the magnetic nanoparticle technology and the molecular imaging technology can be applied to the magnetic induction imaging technology, an unexpected imaging effect can be brought to an existing magnetic induction imaging mode so as to promote great progress of the medical imaging technology.

Embodiment I

Figure 1:
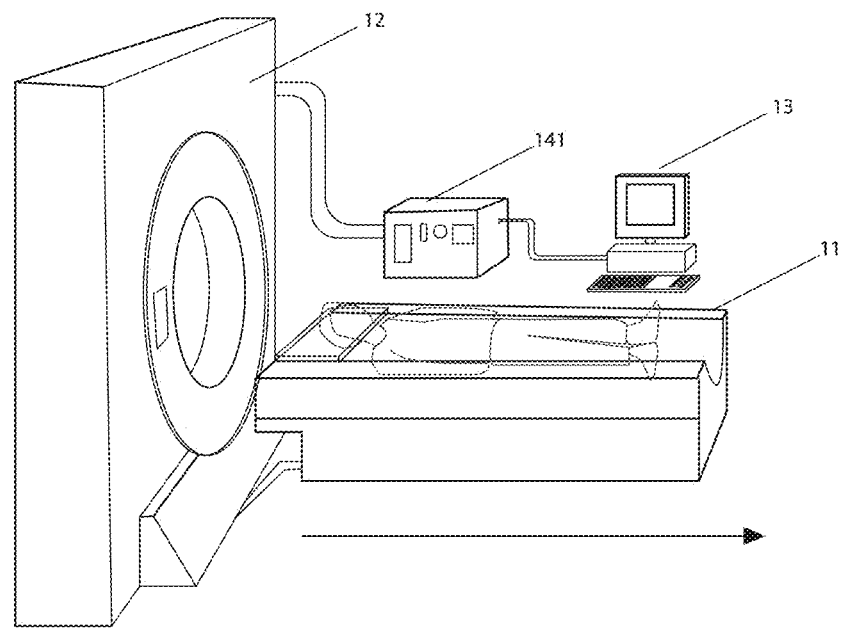
FIG. 1 is a structure diagram of a magnetic induction molecular imaging system for biological tissue detection in the embodiment of the disclosure.

The embodiment of the disclosure provides a magnetic induction molecular imaging system for biological tissue detection, and the system comprises a detection bed, a magnetic nanoparticle device, a magnetic field generating device, a signal receiving and transmitting device, a magnetic field signal acquisition device and computer equipment;

The specific structure is shown in FIG. 1, FIG. 1 shows a position setting relationship among the detection bed 11, the signal receiving and transmitting device 12 and the computer equipment 13, magnetic field equipment is further included, the magnetic field equipment comprises a magnetic field generating device 141 and a magnetic field signal acquisition device (not shown in the figure), and the magnetic nanoparticle device (not shown in the figure) is arranged in the detection bed 11.

The detection bed 11 is used for bearing the weight of a to-be-detected organism.

In some optional embodiments, in order to well position a to-be-detected organ, the detection bed may comprise an organ fixing device, such as a head fixing device, and the specific shape, structure, material, and the like of the organ fixing device are not limited in the embodiment of the disclosure, for example, a head and skull device can be an arc-shaped groove, and the selection is made by those skilled in the art according to actual needs.

The magnetic nanoparticle device comprises a slow-release device, the slow release device is filled with magnetic nanoparticles, and when the to-be-detected organism is measured, the slow release device sends the magnetic nanoparticles to a to-be-detected area of the detection bed, and the magnetic nanoparticles can be ferroferric oxide.

In some optional embodiments, the slow release device may adopt a fiber tube, the upper end and the lower end of the fiber tube are fixed through a support positioning device, the support positioning device comprises a positioning shell fixedly connected with the end of the fiber tube, and the fiber tube is filled with ferroferric oxide.

Figure 2:
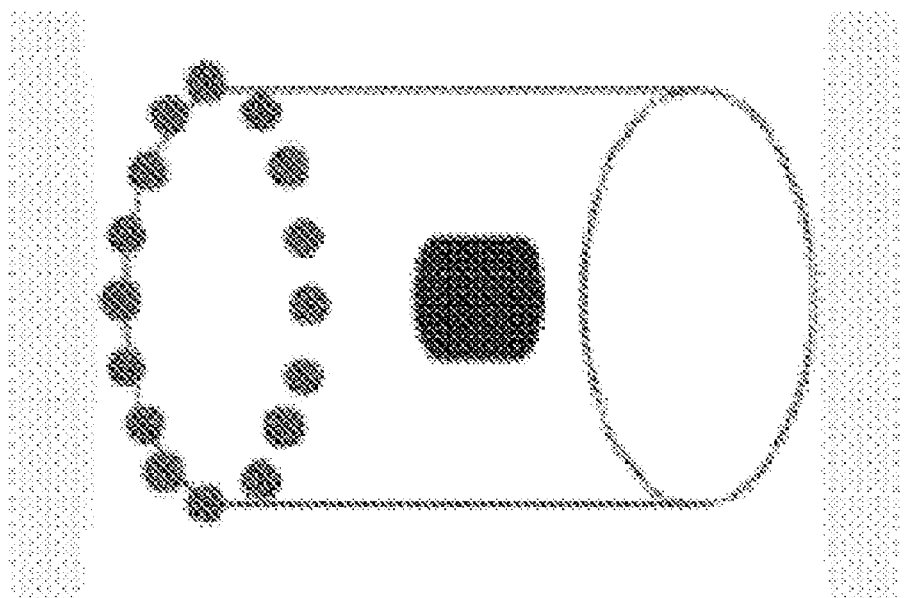
FIG. 2 and FIG. 3 are schematic diagrams of the relative position relation between sensor arrays and a to-be-measured target in a signal receiving and transmitting device in the system shown in FIG. 1.

The magnetic field generating device comprises an electromagnetic wave generating module 141 and Helmholtz coil modules (not shown in the figure), the electromagnetic wave generating module is used for generating and transmitting electromagnetic waves to the signal receiving and transmitting device, and the Helmholtz coil modules are used for generating an excitation magnetic field for the to-be-detected area;

In some optional embodiments, referring to FIG. 2, the number of the Helmholtz coil modules is two, and the two Helmholtz coil modules are symmetrically distributed on the two sides of the sensor arrays.

In some optional embodiments, the electromagnetic wave generating module can, but is not limited to, adopt a vector network analyzer 141, which can generate a radio frequency signal with a frequency range of 1 MHz to 10 MHz.

Figure 3:
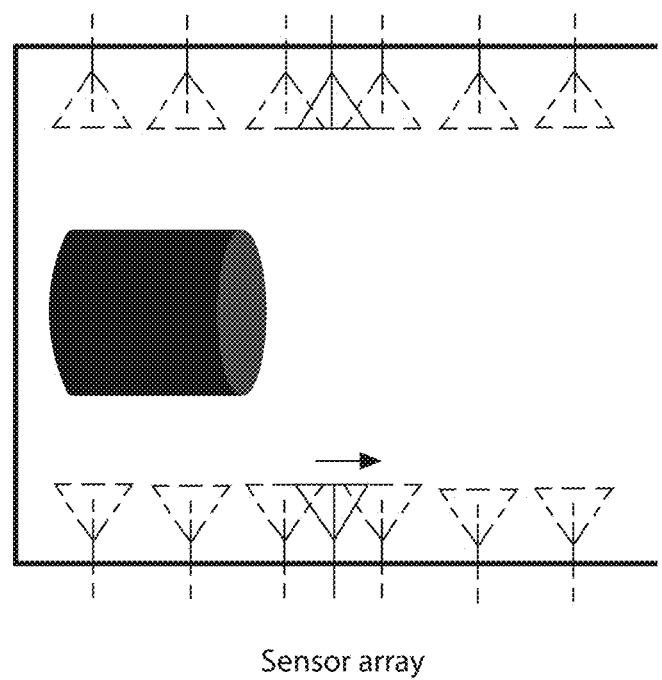

The signal receiving and transmitting device 12, referring to FIG. 2 and FIG. 3, comprises a scanner comprising N sensor arrays, N is a natural number, N is greater than or equal to 3, the distance from the sensor arrays to a to-be-detected organ is far larger than one working wavelength, and sensors are used for receiving the electromagnetic waves transmitted by the magnetic field generating device.

In some optional embodiments, the signal receiving and transmitting device further may comprise an N-channel switch control panel, and a support rotary table module of the sensor arrays, the N-channel switch control panel is used for controlling the sensor arrays, and the support rotary table module is used for bearing the weight of the sensor arrays.

It needs to be explained that the system structure is shown in FIG. 1 is placed according to the position obtained after the system is clockwise rotated by 90 degrees according to the illustrated position in practical application, the human body adopts a sitting posture, the signal receiving and transmitting device can be placed horizontally and move from top to bottom, and in some optional embodiments, at least three sensors on the same plane surround the target area in a uniform arrangement manner and are on the same horizontal plane.

In some optional embodiments, the sensor arrays are implemented by columnar sensor arrays, and all sensors are uniformly distributed in a circular ring shape around a target area by taking the axis of the detection bed as the center and are positioned at the same height and can be formed into columnar sensor arrays, and particularly preferably, the sensors are arranged in a non-uniform shape.

Further optionally, in some optional embodiments, the signal receiving and transmitting device may comprise at least three receiving and transmitting integrated sensors, and the sensors serve as receiving and transmitting sensors of a signal transmitter and a signal detector at the same time; the sensors can adopt but is not limited to, one of a waveguide horn antenna, a patch antenna and a dipole antenna.

For example, in a specific embodiment, the number of the sensors is 16, and the 16 sensors are distributed in a circle around the target object in a non-uniform mode and located at the same height with the target object as the center. Each sensor is used as a magnetic field signal emission sensor to transmit radio frequency waves and is also used as a magnetic field signal detector to acquire magnetic field changes in and around the target object and distribution states of dielectric properties and conductivity.

Preferably, the working frequency of the signal receiving and transmitting device is a single frequency, and the optimal working frequency range of the signal receiving and transmitting device is 1 MHz to 10 MHz. For example, 1 MHz, 2 MHz, 3 MHz, 4 MHz, 5 MHz, 6 MHz, 7 MHz, 8 MHz, or 9 MHz, particularly preferably 2 MHz, may be adopted.

Preferably, in order to reduce the signal coupling and improve the detection sensitivity, the gaps between the target object and the sensors and the gaps between the sensors are filled with medium substances with dielectric properties similar to those of normal fat, such as seawater, saline water, and coconut oil, and the specific filling modes of the medium substances are not limited in the embodiment of the disclosure and are selected as required by those skilled in the art.

The signal receiving and transmitting device can continuously transmit electromagnetic wave signals with specific frequency to the target area to serve as an incident field, and meanwhile, the Helmholtz coil modules can continuously transmit magnetic field signals with a single frequency to the target area to serve as an excitation magnetic field for exciting magnetic nanoparticles in the target area.

After the electromagnetic wave signals penetrate through the target object located in the target area, at least part of the electromagnetic wave signals are reflected by a plurality of parts with different dielectric constants and conductivities in the target object, and then a scattered electromagnetic field is formed, and the scattered field is detected by at least three sensors to obtain scattered field echo signals. The Helmholtz coil modules can transmit excitation magnetic field signals to the target object in the target area so as to apply an external force and receive echo magnetic field signals reflected by the target object so that the magnetic field signal acquisition device can acquire the echo magnetic field signals.

Further optionally, in some optional embodiments, the distance from the sensor arrays to the organ fixing device is much greater than one working wavelength (d being greater than or equal to lambda b), belonging to a far-field microwave working environment.

The magnetic field signal acquisition device may comprise but is not limited to, a data acquisition card, and the data acquisition card is used for acquiring scattered electric field information and scattered magnetic field information, based on the magnetic nanoparticles, of the to-be-detected area detected by each sensor on the sensor arrays and sending the scattered electric field information and the scattered magnetic field information to the computer equipment;

According to the embodiment of the disclosure, the specific implementation modes of the magnetic field signal acquisition device and the signal receiving and transmitting device are not limited, those skilled in the art select the specific implementation modes according to engineering requirements, in some embodiments, a multi-channel control switch circuit board can be arranged, data acquisition of each sensor on the sensor arrays is controlled through the multi-channel control switch circuit, and a power amplifier can be arranged in the signal receiving and transmitting device so as to ensure the intensity of an emitted magnetic field.

The computer equipment 13 is used for analyzing the internal tissue structure state of the to-be-detected organ according to the scattered electric field information and the scattered magnetic field information to form an image.

In some optional embodiments, the computer equipment comprises a processor and a controller, the processor may comprise, but is not limited to, an image processing module, a signal processing module, an information storage module, and an image display module; the signal processing module is used for processing the acquired signals and converting the acquired signals into images; the information storage module is used for storing the acquired signals and the converted image information; the image display module is used for displaying a reconstructed magnetic induction molecular image, the image processing module can be magnetic induction molecular imaging software, and the magnetic induction molecular imaging software can adopt, but is not limited to, MATLAB software or other computer languages to realize an imaging program;

The controller is connected with the magnetic nanoparticle device, the magnetic field generating device, the signal receiving and transmitting device, and the magnetic field signal acquisition device respectively, controls the magnetic nanoparticle device, the magnetic field generating device, the signal receiving and transmitting device and the magnetic field signal acquisition device, and has one or more of the following functions:

firstly, setting one or more of the working frequency, the sampling rate and the sampling speed of the magnetic field generating device and the initial positions of Helmholtz coils;

secondly, setting one or more of the scanning speed, the scanning time, the scanning track mode, and the initial positions of the sensor arrays in the signal receiving and transmitting device;

thirdly, setting one or more of the data acquisition speed, the data acquisition time and the data acquisition mode of the multi-channel control switch circuit board and the data acquisition card in the magnetic field signal acquisition device; and fourthly, setting the administration dosage of the magnetic nanoparticle device.

In some optional embodiments, the signal processing module processes scattered magnetic fields acquired by any two of the at least three sensors and is used for reconstructing a two-dimensional image of the target area containing the magnetic nanoparticles. Preferably, the receiving and transmitting sensor modules are arranged around the target area and located on the same horizontal plane, and the Helmholtz coils are arranged at the top end and the bottom end of the target area.

Specifically, in some optional embodiments, the signal processing module compares the scattered magnetic fields detected by any two sensors in all the sensors to obtain a visibility function; the distribution information capable of reflecting the electromagnetic property and conductivity of the target object are obtained according to the visibility function obtained by comparison; and the visibility function is processed through inverse Fourier transform to reconstruct the magnetic induction molecular image of the target object.

Further specifically, in some optional embodiments, the signal processing module establishes a nonlinear observation model between the electromagnetic property of the target object and the scattered magnetic fields based on the distribution shape of the sensor arrays; and/or the scattered echo signals and/or the scattered magnetic fields are compared pairwise at least partially based on the nonlinear observation model.

Wherein the signal processing module comprises, but is not limited to, the following functional units:

an independent visibility function calculation unit is used for calculating visibility functions of any two receiving and transmitting sensors by calculating scattered magnetic field signals acquired by any two receiving and transmitting sensors on the same plane; specifically, the scattered magnetic field information detected by any two sensors, of magnetic nanoparticles in the to-be-detected area containing the magnetic nanoparticles can be extracted, and the differences of the scattered magnetic field information detected by the two sensors are compared to obtain the visibility function:

$$\Delta \vec{H}_{scat}(\vec{r}_i, \vec{r}_j) = \langle \vec{H}_{scat}(\vec{r}_i) \cdot \vec{H}_{scat}(\vec{r}_j) \rangle \tag{16}$$

In formula (16), $\Delta \vec{H}_{scat}(\vec{r}_i, \vec{r}_j)$ represents that the visibility function of the two sensors located at the positions of $(\vec{r}_i, \vec{r}_j)$ comprises phase delay and/or amplitude difference information, $\vec{r}_i$ represents the distance vector from any point of the target area to the i-th sensor, $\vec{r}_j$ represents the distance vector from any point of the target area to the j-th sensor, $\vec{H}_{scat}(\vec{r}_i)$ represents a scattered magnetic field detected by the sensor located at the position of $\vec{r}_i$, and $\vec{H}_{scat}(\vec{r}_i)\vec{H}_{scat}^*(\vec{r}_j)$ represents the conjugate of the scattered magnetic field detected by the sensor located at the position of $\vec{r}_j$, *represents complex conjugate, and < > represents average time;

a total visibility function calculation unit is used for extracting the magnetization information and the scattered electric field information of the magnetic nanoparticles in the to-be-detected area detected by all the sensors and comparing information differences detected by any two sensors one by one to obtain the sum of visibility functions including phase delay and/or amplitude difference information, namely the total visibility function:

$$Y = \Sigma_i^N \Delta \vec{H}_{scat}(\vec{r}_i, \vec{r}_j), i=1, \ldots, N; N \geq 3, a \neq b \quad (17)$$

Y represents the total visibility function of all sensors, N represents the total number of the sensors, $\Delta \vec{E}_{scat}(\vec{r}_i, \vec{r}_j)$ represents that the visibility function of the two sensors located at the positions of $\vec{r}_i$, $\vec{r}_j$ comprises phase delay and/or amplitude difference information as well as the magnetization intensity of the internal tissue.

a model description unit is used for defining a nonlinear observation model of visibility intensity of the target object as follows:

$$I(\vec{s}) = \left(\frac{j\omega\mu_0}{4\pi}\right)^2 |\sigma(\vec{s}) + j\omega\varepsilon_0\varepsilon_r|^2 \overrightarrow{H_T}(\vec{s}) \cdot \overrightarrow{H_T}(\vec{s'}) \quad (18)$$

In formula (18), j is a complex imaginary part, $j=\sqrt{-1}$, the working angular frequency is that $\omega=2\pi f$, f is the working frequency of the imaging system, $\mu_0$ is the magnetic permeability of the free space, $\sigma$ is the electrical conductivity of the target organism, $\varepsilon_0$ is the dielectric constant of the free space, $\varepsilon_r$ is the dielectric constant of the target organism, $\varepsilon_r = \varepsilon_r' - j\sigma/\omega\varepsilon_0$, $\varepsilon_r'$, $\varepsilon_r'$ is the real part of the relative dielectric constant of the target organism, $\overrightarrow{H_T}$ is the total magnetic field, and $\overrightarrow{H_T}$ represents incident field plus scattered field; the nonlinear observation model comprises an internal field effect model and an external field effect model;

the internal magnetic field induction model is described as follows:

$$\overrightarrow{H_r}(\vec{r}) = \overrightarrow{H_{inc}}(\vec{r'}) - \frac{j}{4\pi\omega\mu_0} \int_V \left[(\overrightarrow{J_m} \cdot \nabla)\nabla + k_0^2 \overrightarrow{J_m} + j\omega\mu_0 \vec{J}_s \times \nabla\right] G(\vec{r}, \vec{r'}) dV \quad (19)$$

In formula (19), $\overrightarrow{H_{inc}}$ is an incident magnetic field, G is a Green function, $\vec{r'}$ is a position vector from a field source point to the scattered magnetic field, $\vec{r}$ is a position vector from the field source point to a point in the target organism, $k_0$ is the wavenumber of the free space, $\overrightarrow{J_m}$ is magnetic current density, $\overrightarrow{J_m} = j\omega\mu_0(\mu_r-1)\overrightarrow{H_T}$, $\mu_r$ is the magnetic permeability of the target organism, $\vec{J}_s$ is induced current density, $\vec{J}_s = j\omega\varepsilon_0(\varepsilon_r-1)\vec{E}$, $\vec{E}$ is a total electric field, and $\vec{E}$ is the incident electric field plus the scattered electric field;

the external magnetic field induction model is described as follows:

$$\vec{H}_{scat}(\vec{r_0}) = \frac{k_0^2}{4\pi} \int_V \left[(a\vec{H} + b(\vec{H} \cdot \hat{r})\hat{r})\right] G(\vec{r}, \vec{r_0}) dV \quad (20)$$

In formula (20), $\vec{H}_{scat}$ is the scattered magnetic field, $\hat{r}$ is a unit vector from the field source point to any point in a field domain, $$a = \mu_r \varepsilon_r - 1 - \frac{(\mu_r - 1)j}{k_0 R}\left(1 - \frac{j}{k_0 R}\right),$$

$$b = (\mu_r - 1)\left(-1 + \frac{3j}{k_0 R} + \frac{3}{(k_0 R)^2}\right),$$

and R is the distance from the field source point to any point in the scattered field. $k_0^2 a \cong -(\mu_r-1)/R^2$, $k_0^2 b \cong 3(\mu_r-1)/R^2$.

The image processing module comprises, but is not limited to, a two-dimensional image processing unit, and the two-dimensional image processing unit constructs a two-dimensional image of the target object through an inverse Fourier transform processing mode based on the amplitude and phase of the dielectric property and the conductivity distribution and the information of the magnetic susceptibility intensity of the internal tissue; specifically, two-dimensional inverse Fourier transform can be carried out on visibility function signals acquired by any two sensors to obtain a two-dimensional reconstructed image of the target object:

$$\tilde{I} = \iint Y(\vec{r}_i, \vec{r}_j) e^{-j2\pi(u_{ij}l + v_{ij}m)} du dv \quad (21)$$

Wherein, $Y(\vec{r}_i, \vec{r}_j)$ represents that the visibility functions of the two sensors located at the positions of $(\vec{r}_i, \vec{r}_j)$ comprise phase delay and/or amplitude difference information and the magnetic susceptibility intensity of the internal tissue, $l=\sin\theta\cos\phi$, $m=\sin\theta\sin\phi$, $u_{ij}=(\overline{x_j}-\overline{x_i})/\lambda_b$, $v_{ij}=(\overline{y_j}-\overline{y_i})/\lambda_b$, $\hat{x}$, $\hat{y}$ and $\hat{z}$ are unit vectors along with the positive time-space directions of the x-axis, the y-axis, and the z-axis, respectively, $\overline{x_i}$ $\overline{y_i}$ $\overline{z_i}$ are the positions of any sensor $A_i$ in the rectangular coordinate system along the x-axis, the y-axis, and the z-axis, respectively, $\overline{x_j}$ $\overline{y_j}$ $\overline{z_j}$ are the positions of any sensor $A_j$ in the rectangular coordinate system along the x-axis, the y-axis, and the z-axis respectively, $\phi$ is an included angle between the connecting line of an original point O and any point P in the space and the forward z-axis, $\phi$ is an included angle between the xoz plane and a half-plane passing through any point P in the space, and if the point P is on the z-axis, the $\phi$ angle is uncertain. $\hat{s} = \sin\theta\cos\phi\hat{x} + \sin\theta\sin\phi\hat{y} + \cos\theta\hat{z}$, $\lambda_b$ represents the wavelength of a background/medium.

According to the magnetic induction molecular imaging system for biological tissue detection provided by the embodiment of the disclosure, organism detection is carried out by utilizing the imaging property of the magnetic nanoparticles and the dielectric property of the biological tissue, and the basic principle is as follows: according to different magnetic susceptibilities of various different magnetic nanoparticles, strain is different after an external magnetic field or alternating vibration is applied, the change of magnetic susceptibility is different mainly, and scattered magnetic fields of target biological tissues are different under the irradiation of the electromagnetic waves according to different dielectric properties and conductivities of different biological tissues, so that the appearance image of the target or the structural imaging in the medium target can be reconstructed by analyzing and processing the morphological change and the scattered magnetic field, the spatial magnetic field distribution can also be visually displayed, compared with fusion imaging, the imaging speed is higher, the imaging quality is better, and the system can be used for the fields of biomedical imaging, disease diagnosis, foreign matter detection and the like.

Embodiment II

Figure 4:
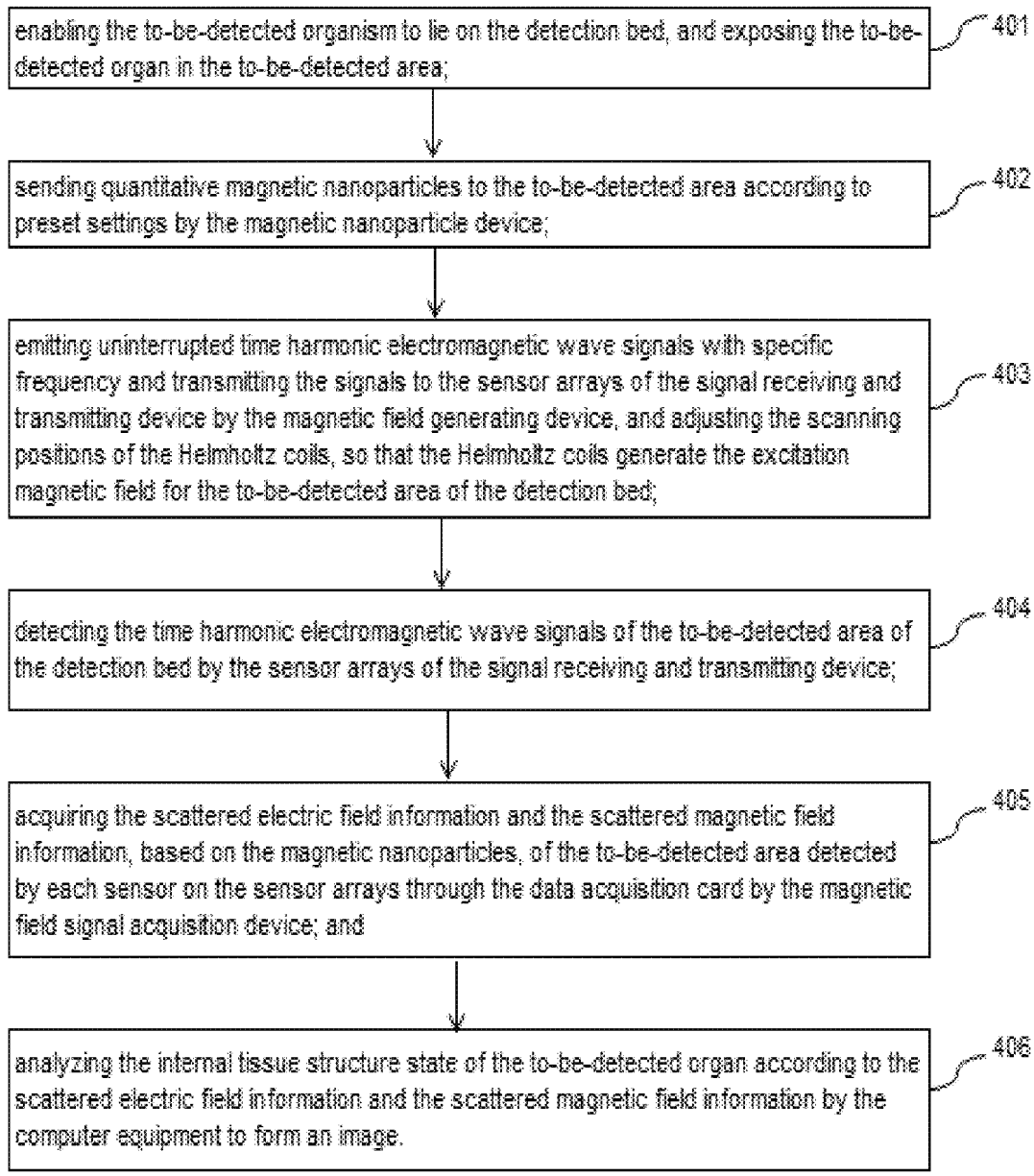
FIG. 4 is a process diagram of a magnetic induction molecular imaging method for biological tissue detection in the embodiment of the disclosure.
Figure 5:
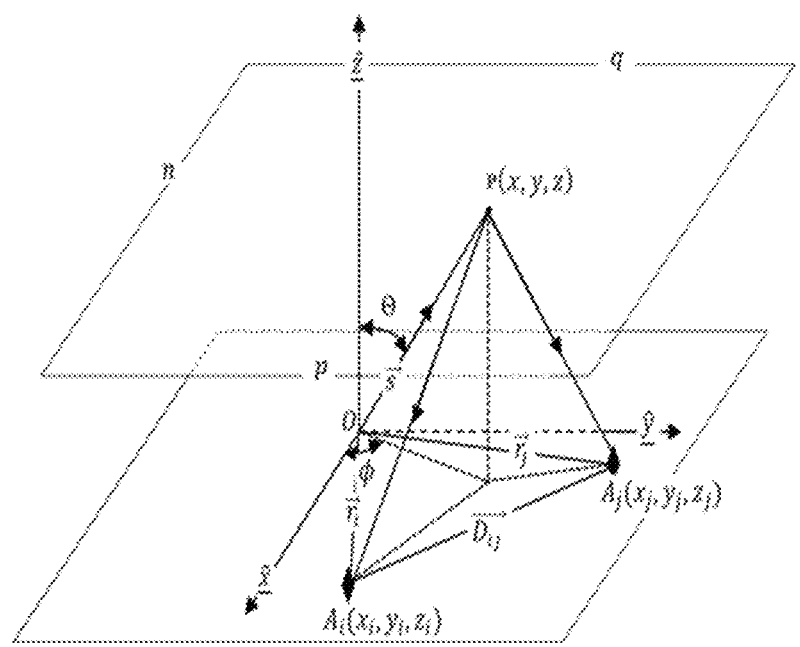
FIG. 5 to FIG. 18 are schematic diagrams of calculation principles and related images when the system is shown in FIG. 1 is applied to detect the brain.
Figure 6:
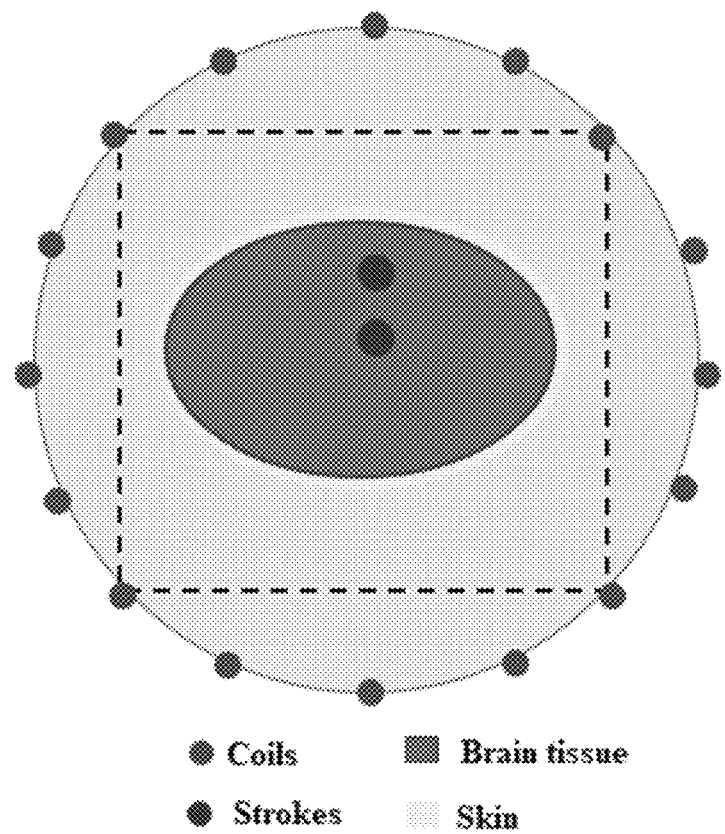
Figure 7:
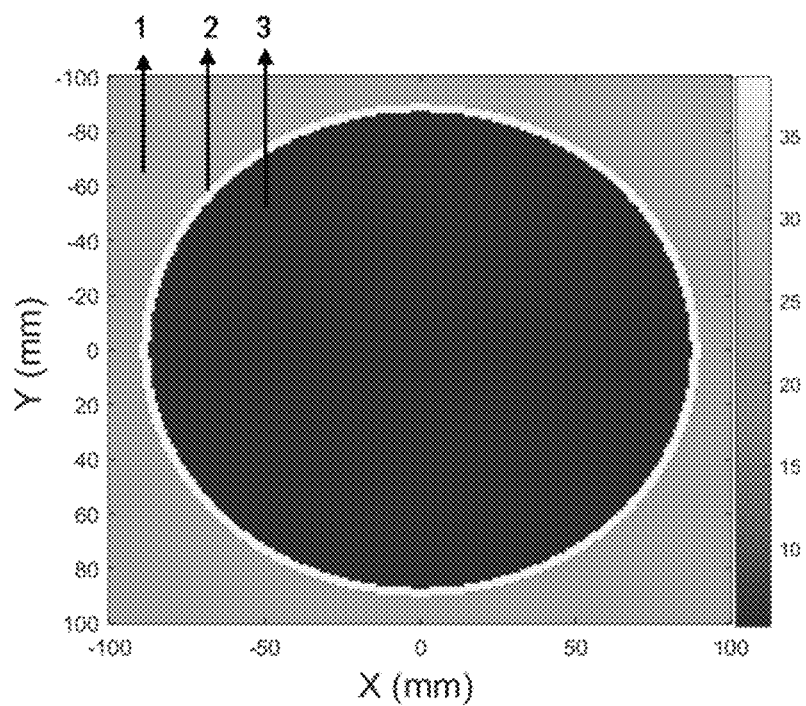
Figure 8:
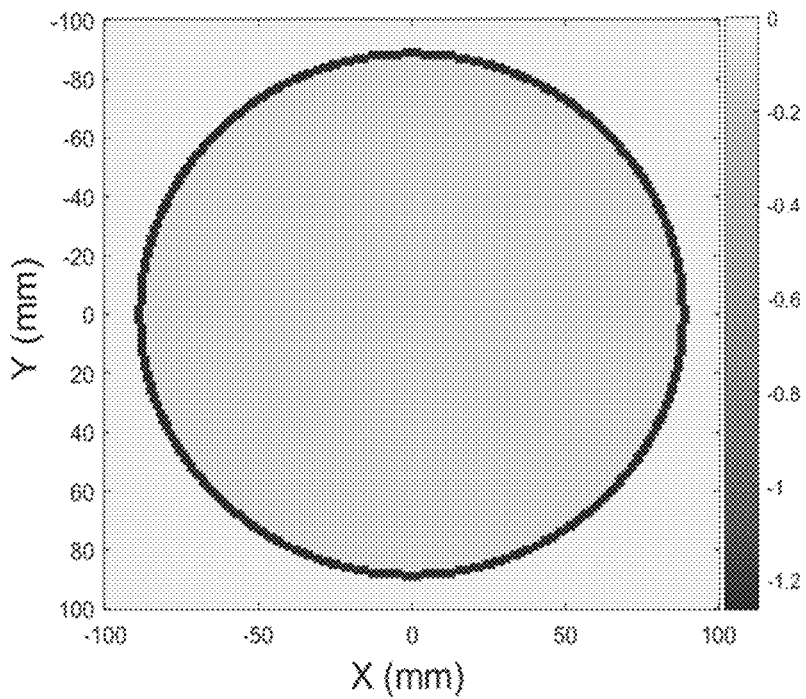
Figure 9:
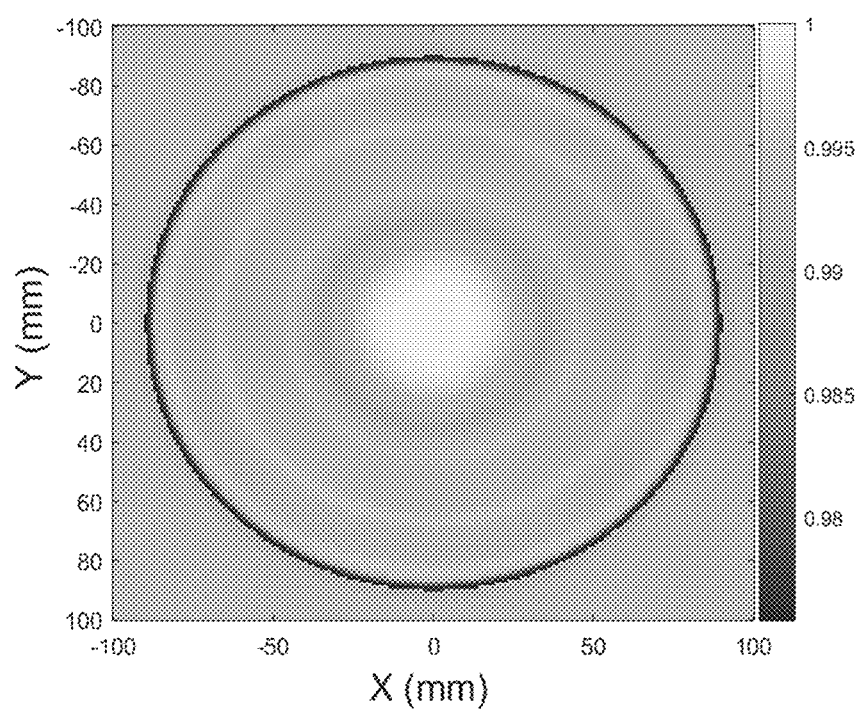
Figure 10:
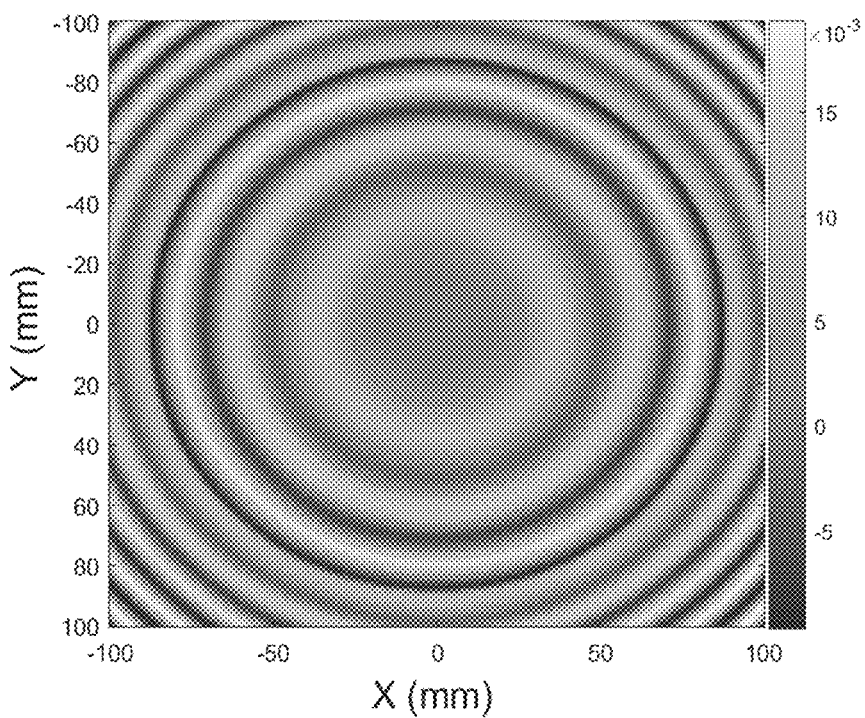
Figure 11:
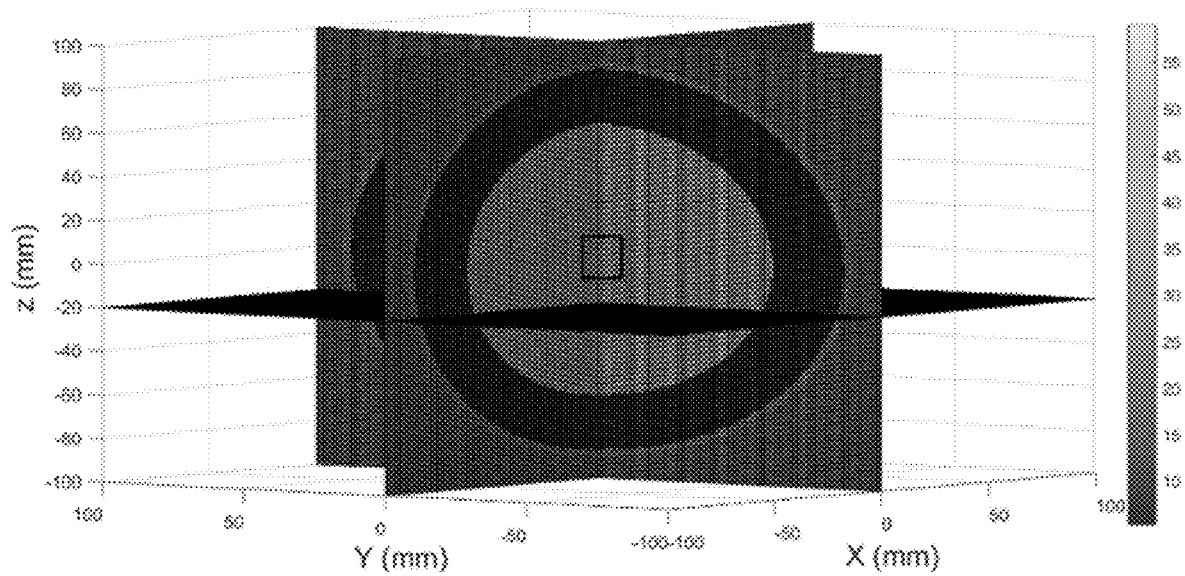
Figure 12:
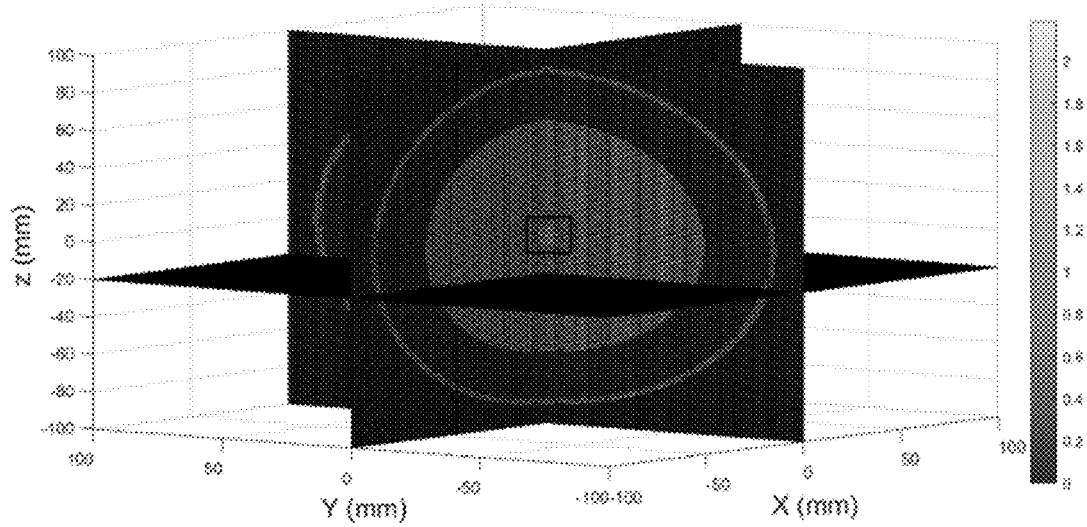
Figure 13:
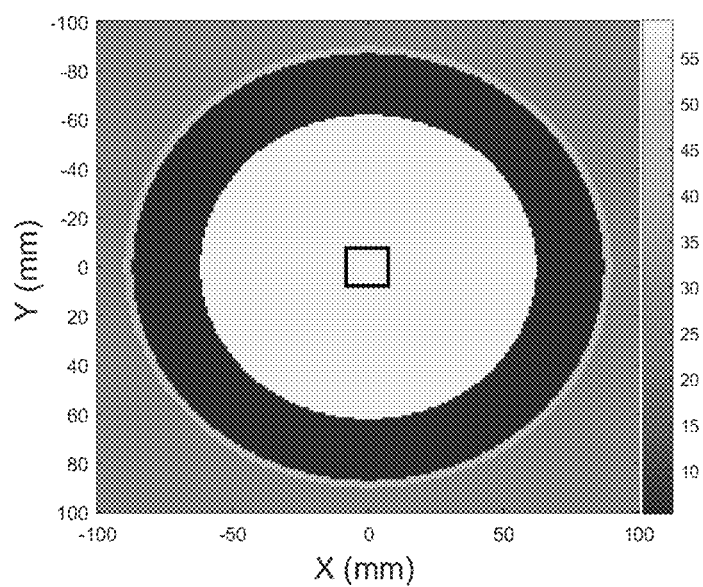
Figure 14:
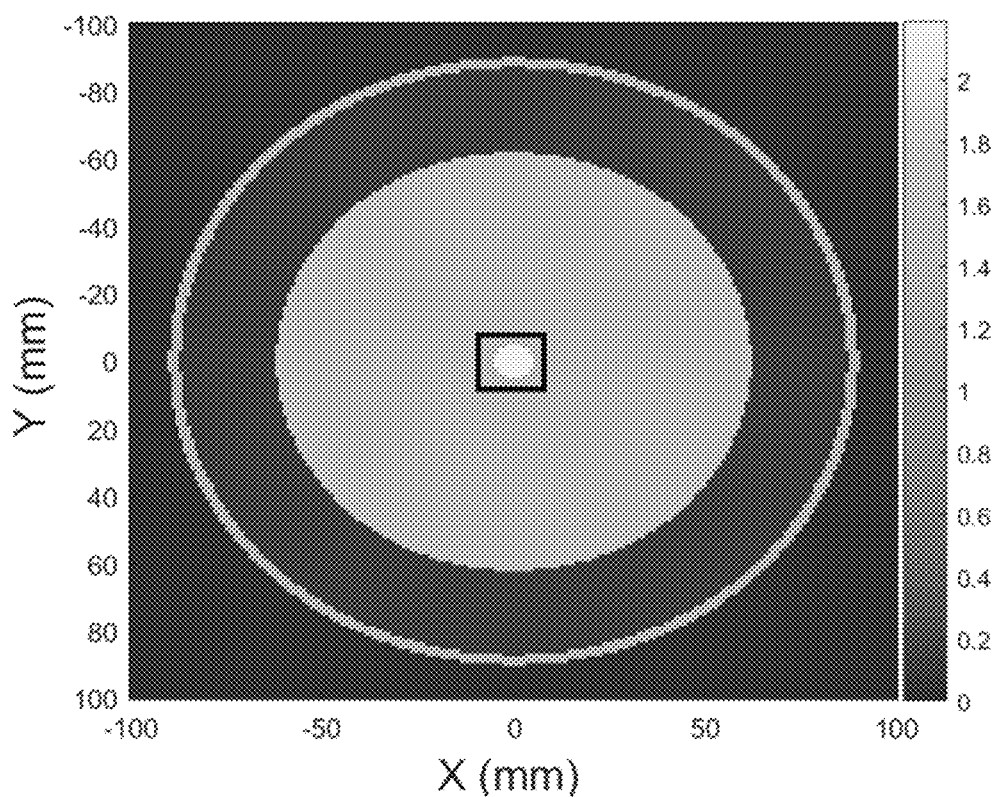
Figure 15:
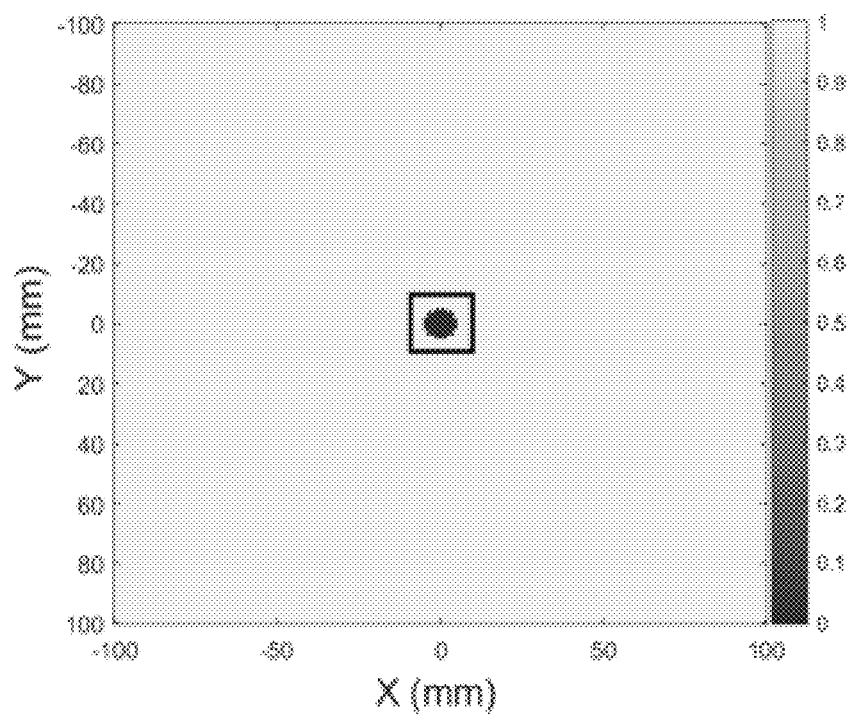
Figure 16:
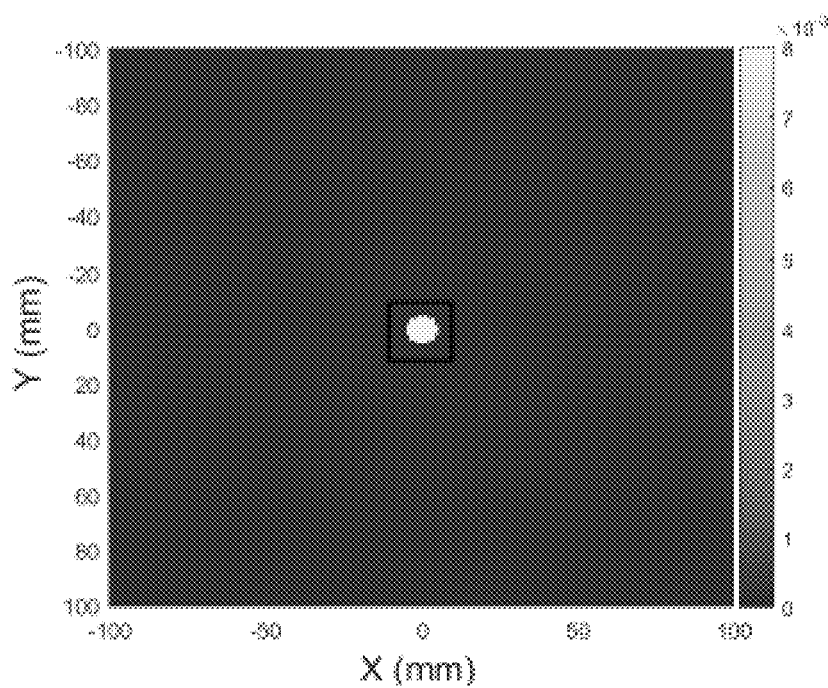
Figure 17:
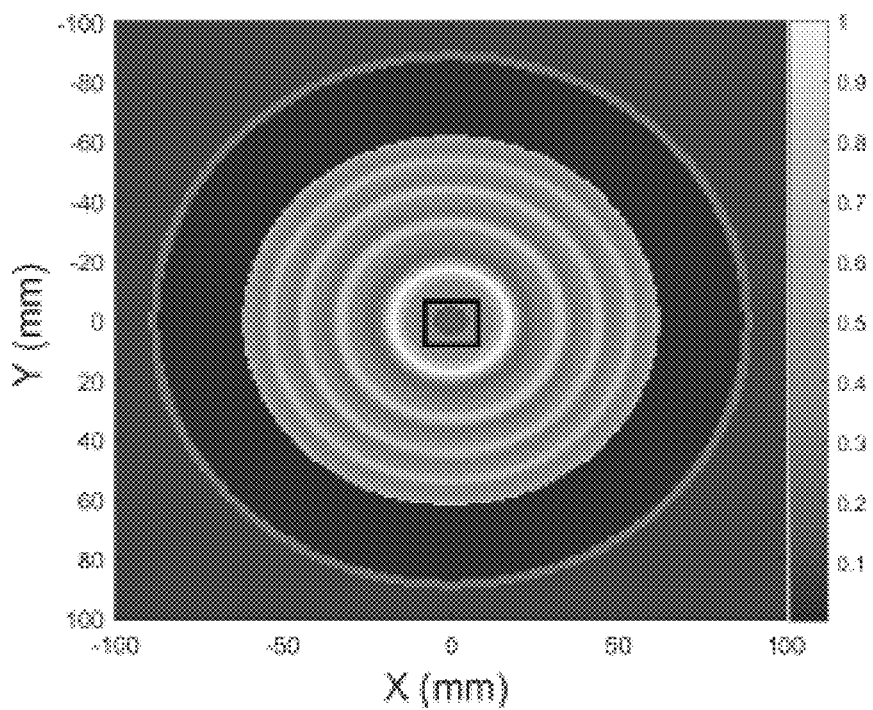
Figure 18:
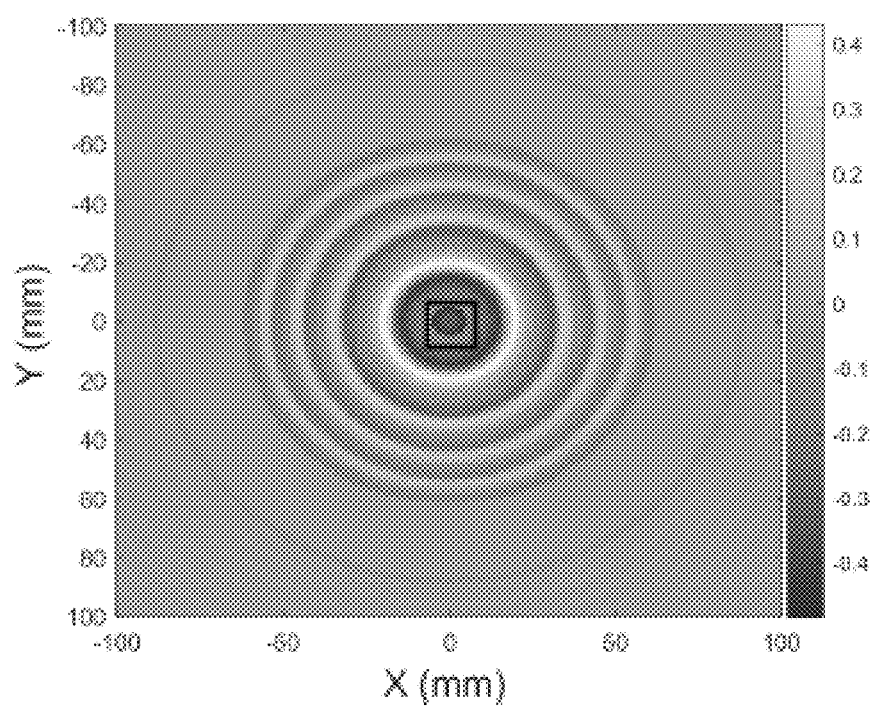

Based on the magnetic induction molecular imaging system for biological tissue detection, according to the magnetic induction molecular imaging method for biological tissue detection provided by the embodiments of the disclosure, referring to FIG. 4, the method comprises, but is not limited to, the following processes:

401, enabling the to-be-detected organism to lie on the detection bed, and exposing the to-be-detected organ in the to-be-detected area;

402, sending quantitative magnetic nanoparticles to the to-be-detected area according to preset settings by the magnetic nanoparticle device;

403, emitting uninterrupted time-harmonic electromagnetic wave signals with a specific frequency and transmitting the signals to the sensor arrays of the signal receiving and transmitting device by the magnetic field generating device, and adjusting the scanning positions of the Helmholtz coils so that the Helmholtz coils generate the excitation magnetic field for the to-be-detected area of the detection bed;

404, detecting the time-harmonic electromagnetic wave signals of the to-be-detected area of the detection bed by the sensor arrays of the signal receiving and transmitting device;

405, acquiring the scattered electric field information and the scattered magnetic field information, based on the magnetic nanoparticles, of the to-be-detected area detected by each sensor on the sensor arrays through the data acquisition card by the magnetic field signal acquisition device; and 406, analyzing the internal tissue structure state of the to-be-detected organ according to the scattered electric field information and the scattered magnetic field information by the computer equipment to form an image.

Specifically, in some optional embodiments, the computer constructs a two-dimensional image of the target object through the inverse Fourier transform processing mode based on the amplitude and the phase of the dielectric property and the conductivity distribution of the biological tissue and the magnetic susceptibility intensity information of the internal tissue.

Further specifically, in some optional embodiments, the computer performs a two-dimensional inverse Fourier transform on the visibility function signals acquired by any two sensors to obtain the two-dimensional reconstructed image of the target object.

Further specifically, in some optional embodiments, the acquisition of the visibility function comprises, but is not limited to, the following process:

firstly, extracting the scattered magnetic field information of the magnetic nanoparticles in the to-be-detected area containing the magnetic nanoparticles detected by any two sensors; and secondly, comparing differences of the scattered magnetic field information detected by the two sensors to obtain the visibility function of the two sensors.

Further specifically, in some optional embodiments, the acquisition process of the visibility function comprises, but is not limited to, the following process:

firstly, extracting the magnetization information and the scattered electric field information, detected by all the sensors, of the magnetic nanoparticles in the to-be-detected area; and secondly, comparing information differences detected by any two sensors one by one to obtain the sum of visibility functions, including phase delay and/or amplitude difference information, namely a total visibility function.

According to the magnetic induction molecular imaging method for biological tissue detection provided by the embodiment of the disclosure, organism detection is carried out by utilizing the imaging property of the magnetic nanoparticles and the dielectric property of the biological tissue, and the basic principle is as follows: according to different magnetic susceptibilities of various different magnetic nanoparticles, strain is different after an external magnetic field or alternating vibration is applied, the change of magnetic susceptibility is different mainly, and the scattered magnetic fields of target biological tissues are different under the irradiation of the electromagnetic waves according to different dielectric properties and conductivities of different biological tissues, so that the appearance image of the target or the structural imaging in the medium target can be reconstructed by analyzing and processing the morphological change and the scattered magnetic fields, the spatial magnetic field distribution can also be visually displayed, compared with fusion imaging, the imaging speed is higher, the imaging quality is better, and the method can be used for the fields of biomedical imaging, disease diagnosis, foreign matter detection and the like.

Embodiment III

In order to facilitate understanding by the reader, based on the magnetic induction molecular imaging method for biological tissue detection, a specific embodiment is provided below, referring to FIG. 5 to FIG. 18, the method comprises the processes:

S1, enabling a to-be-detected human body to lie on the detection bed in a supine mode, and placing the to-be-detected organ (such as the head) on the organ fixing device;

S2, setting the following parameters by a controller within the computer equipment:

S21, one or more of the working frequency, the sampling rate and the sampling speed of the magnetic field generating device and the initial positions of Helmholtz coils;

S22, one or more of the scanning speed, the scanning time, the scanning track mode, and the initial positions of the sensor arrays in the signal receiving and transmitting device;

S23, one or more of the data acquisition speed, the data acquisition time and the data acquisition mode of the multi-channel control switch circuit board and the data acquisition card in the magnetic field signal acquisition device;

S24, the administration dosage of the magnetic nanoparticle device;

S3, sending quantitative magnetic nanoparticles to the to-be-detected area according to settings by the magnetic nanoparticle device;

Wherein, the magnetic nanoparticles can be seen as a ferromagnetic fluid, and a Brownian relaxation phenomenon caused by mechanical rotation can be expressed as follows:

$$\tau_B = \frac{3\eta V_H}{k_b T} \quad (1)$$

In formula (1), $\eta$ is the viscosity of the liquid-carrying ferromagnetic fluid, and $V_H$ is the hydrodynamic volume of the magnetic nanoparticles.

The relaxation time of the magnetization decay of the ferromagnetic fluid is as follows:

$$\tau_{\mathit{eff}} = \frac{\tau_N \tau_B}{\tau_N + \tau_B} \quad (2)$$

The complex sensitivities of ferromagnetic fluid can be defined as follows:

$$x_\mu(\omega) = \frac{1}{3}[x_\parallel(\omega) + 2x_\perp(\omega)] \quad (3)$$

In formula (3), $x_\parallel$ and $x_\perp$ are the parallel magnetic susceptibility and the transverse magnetic susceptibility respectively, $x_\parallel$ is related to the low frequency (relaxation mechanism) contribution, and $x_\perp$ is related to the high-frequency (ferromagnetic resonance) contribution. The system of the disclosure adopts a lower working frequency (lower GHz range) and can ignore the parallel magnetic susceptibility, and thus, $x_\mu$, can be expressed by the following formula:

$$x_\mu(\omega) \approx \frac{2}{3} x_\perp(\omega) = \frac{2}{3} x_0 \frac{1 + (\omega_0 \tau_0)^2 + i\omega\tau_0}{1 + (\omega_0 \tau_0)^2 - (\omega\tau_0)^2 + 2i\omega\tau_0} \quad (4)$$

in formula (4), $x_0$ is static transverse magnetic susceptibility, $\tau_0$ is characteristic time, $\omega$ is the angular frequency, $\omega_0 = \gamma H_a$, wherein $\gamma$ is a gyromagnetic ratio, $H_a$ is an anisotropy field $H_a = 2K_d/(\mu_0 M_s)$, and $\mu_0$, is the magnetic conductivity of the free space.

When a polarized magnetic field with an amplitude h is superimposed to the time-harmonic electromagnetic field, the formula (4) is valid, and the time-harmonic electromagnetic field changes as a result of the changes of $x_0$ and $\omega_0$. For example, when $\omega_0$ is increased, $$\omega_0(H) = \gamma(H_a + H) \quad (5)$$

$x_0$ is reduced.

$$x_0(H) = \frac{cM^2 V_m \mu_0}{k_b T}\left[\frac{\coth\left(\frac{mH}{k_b T}\right)}{\frac{mH}{k_b T}} - \frac{1}{\left(\frac{mH}{k_b T}\right)^2}\right] \quad (6)$$

In formula (5), m is the magnetic moment amplitude of the magnetic nanoparticles, and c is the volume concentration of the magnetic nanoparticles.

S4, emitting uninterrupted time-harmonic electromagnetic wave signals with a specific frequency and transmitting the signals to the sensor arrays of the signal receiving and transmitting device by the magnetic field generating device; and simultaneously, generating the excitation magnetic field for the to-be-detected area of the detection bed through the Helmholtz coils by the device; wherein the incident electric field may be described as follows:

(7)

$$\vec{E}_{inc}(\vec{r}) = \vec{E}(\vec{r}) - \left\{[k_b^2 + \nabla\nabla\cdot]\int_V G(\vec{r},\vec{r}')\Delta x_E(\vec{r}')\vec{E}(\vec{r}')dV - \right. \\ \left. j\omega\mu_b\nabla\times\int_V G(\vec{r},\vec{r}')\Delta x_H(\vec{r}')\vec{H}(\vec{r}')dV\right\} \quad (7)$$

wherein the incident magnetic field may be described as follows:

(8)

$$\vec{H}_{inc}(\vec{r}) = \vec{H}(\vec{r}) - \left\{[k_b^2 + \nabla\nabla\cdot]\int_V G(\vec{r},\vec{r}')\Delta x_H(\vec{r}')\vec{H}(\vec{r}')dV - \right. \\ \left. j\omega\tilde{\varepsilon}_b\nabla\times\int_V G(\vec{r},\vec{r}')\Delta x_E(\vec{r}')\vec{E}(\vec{r}')dV\right\} \quad (7)$$

In the formula, $\vec{r}$ is the sensor and/or the coil located at the position of $\vec{r}$, $\vec{r}'$ is the sensor and/or the coil located at the position of $\vec{r}'$, $\omega$ represents angular frequency, $k_b$ and $\mu_b$ represent wave number and magnetic conductivity of a background respectively, $G(\vec{r},\vec{r}')$ represents a Green formula, $G(\vec{r},\vec{r}') = e^{-jk_b|\vec{r}-\vec{r}'|}/4\pi|\vec{r}-\vec{r}'|$, $\Delta x_E$ and $\Delta x_H$ represent electrical contrast and magnetic contrast respectively, $\Delta x_E = (\tilde{\varepsilon}(\vec{r}) - \tilde{\varepsilon}_b)/\tilde{\varepsilon}_b$, $\Delta x_H = (\mu(\vec{r}) - \mu_b)/\mu_b$, $\tilde{\varepsilon}(\vec{r})$ represents a complex dielectric constant of the target object, $\tilde{\varepsilon}(\vec{r}) = \varepsilon(\vec{r}) - j\sigma(\vec{r})/\omega$, $\tilde{\varepsilon}_b$ represents the complex dielectric constant of the background, $\tilde{\varepsilon}(\vec{r}) = \varepsilon(\vec{r}) - j\sigma(\vec{r})/\omega$, $\varepsilon_b$ represents the relative dielectric constant of the background, $\sigma_b$ and $\sigma$ represent the electrical conductivities of the background and the target object respectively, $\mu_b$, and $\mu$. represent the permeability of the background and the target object, $\vec{E}_{inc}$ represents the incident electric field irradiated to the target object, and represents the excitation magnetic field introduced into the target object.

S5, transmitting the time-harmonic electromagnetic wave signals to the to-be-detected area of the detection bed by the sensor arrays; and the formulas (7) and (8) may be simplified as follows:

(9)

$$\vec{E}_{inc}(\vec{r}) = \vec{E}(\vec{r}) + j\omega\vec{A}(\vec{r}) + \frac{j\omega}{k_b^2}\nabla\nabla\cdot\vec{A}(\vec{r}) + \frac{\nabla\times\vec{F}(\vec{r})}{\tilde{\varepsilon}_b} \quad (7)$$

(10)

$$\vec{H}_{inc}(\vec{r}) = \vec{H}(\vec{r}) + j\omega\vec{F}(\vec{r}) - \frac{j\omega}{k_b^2}\nabla\nabla\cdot\vec{F}(\vec{r}) + \frac{\nabla\times\vec{A}(\vec{r})}{\mu_b} \quad (7)$$

Wherein magnetic vector potential is that $\vec{A}(\vec{r}) = j\omega\mu_b\tilde{\varepsilon}_b\int_V G(\vec{r},\vec{r}')\Delta x_E(\vec{r}')E(\vec{r}')dV$, and the vector potential is that $\vec{F}(\vec{r}) = j\omega\mu_b\tilde{\varepsilon}_b\int_V G(\vec{r},\vec{r}')\Delta x_H(\vec{r}')\vec{H}(\vec{r}')dV$.

S6, controlling the scanning positions of the Helmholtz coils by the controller, controlling the rotating speeds, the scanning speeds, and the scanning tracks of the sensor arrays by the signal receiving and transmitting device, and acquiring the scattered electric field information and the scattered magnetic field information, detected by each sensor on the sensor arrays, based on the magnetic nanoparticles in the to-be-detected area through the data acquisition card;

(11)

$$\vec{E}_{scat}(\vec{r_i}) = \int_V (k_b^2 + \nabla\nabla\cdot)G(\vec{r_i},\vec{r}')\Delta x_E(\vec{r}')\vec{E}(\vec{r}',\vec{r_t})dV - \quad (7)$$

$$j\omega\mu_b\int_V \nabla\times G(\vec{r_{ii}},\vec{r}')\Delta x_H(\vec{r}')\vec{H}(\vec{r}',\vec{r_t})dV$$

(12)

$$\vec{H}_{scat}(\vec{r_i}) = \int_V (k_b^2 + \nabla\nabla\cdot)G(\vec{r_i},\vec{r}')\Delta x_H(\vec{r}')\vec{H}(\vec{r}',\vec{r_t})dV + \quad (7)$$

$$j\omega\varepsilon_b\int_V \nabla\times G(\vec{r_i},\vec{r}')\Delta x_E(\vec{r}')\vec{E}(\vec{r}',\vec{r_t})dV$$

Wherein $\vec{r_i}$ represents a transceiver located at the position of $\vec{r_i}$, and the formula may be expressed as follows:

(13)

$$\vec{E}_{scat}(\vec{r_i}) = k_b^2\int_V G_b^E(\vec{r_i},\vec{r}')\Delta x_E(\vec{r}')\vec{E}(\vec{r_i},\vec{r_t})dV - \quad (7)$$

$$j\omega\mu_b\int_V G_b^H(\vec{r_i},\vec{r}')\Delta x_H(\vec{r}')\vec{H}(\vec{r}',\vec{r_t})dV$$

(14)

$$\vec{H}_{scat}(\vec{r_i}) = k_b^2\int_V G_b^E(\vec{r_i},\vec{r}')\Delta x_H(\vec{r}')\vec{H}(\vec{r_i},\vec{r_t})dV + \quad (7)$$

$$j\omega\varepsilon_b\int_V G_b^H(\vec{r_i},\vec{r}')\Delta x_E(\vec{r}')\vec{E}(\vec{r}',\vec{r_t})dV$$

In the formula, $G_b^E(\vec{r_i}\,r')$ and $G_b^H(\vec{r_i}\,r')$ represent a scattered electric field vector Green function and a scattered magnetic field vector Green function respectively, $$G_b^E(\vec{r_i},\vec{r}') =$$

$$\frac{e^{-jk_bR}}{4\pi R^3}\begin{bmatrix} h_1+(x-x')^2h_2 & (x-x')(y-y')h_2 & (x-x')(z-z')h_2 \\ (x-x')(y-y')h_2 & h_1+(y-y')^2h_2 & (y-y')(z-z')h_2 \\ (x-x')(z-z')h_2 & (y-y')(z-z')h_2 & h_1+(z-z')^2h_2 \end{bmatrix}$$

$$G_b^H(\vec{r_i},\vec{r}') = -\frac{(1+jk_bR)e^{-jk_bR}}{4\pi R^3}\begin{bmatrix} 0 & -(z-z') & (y-y') \\ (z-z') & 0 & -(x-x') \\ -(y-y') & (x-x') & 0 \end{bmatrix}$$

$$R=|\vec{r_i}-\vec{r}'|,\, h_1=R^2\left(1+\frac{1}{jk_bR}-\frac{1}{(k_bR)^2}\right),\, h_2=-1-\frac{3}{jk_bR}+\frac{3}{(k_bR)^2}.$$

The formulas (13) and (14) may be used for simulating the scattered electromagnetic field if the working frequency of the imaging system remains relatively low. The electrical conductivity of the biological tissue is relatively small compared with good conductive materials (e.g., metals). The Bone approximation can be used for solving the electromagnetic positive problem. Therefore, the electromagnetic field inside the object can be seen approximately as an incident field when present at the same location without the placement of the target object. The formula (13) can be expressed as follows:

(15)

$$\vec{E}_{scat}(\vec{r_i}) = k_b^2\int_V G_b^E(\vec{r_i},\vec{r}')\Delta x_E(\vec{r}')\vec{E}_{inc}(\vec{r_i},\vec{r}')dV - \quad (7)$$

$$j\omega\mu_b\int_V G_b^H(\vec{r_i},\vec{r}')\Delta x_H(\vec{r}')\vec{H}_{inc}(\vec{r_i},\vec{r}')dV$$

The scattered electric field is much smaller than the incident electric field when the magnetic permeability of the magnetic nanoparticles is much smaller than that of the object. If the scattered field can be extracted from the incident field, the image of the target area containing the magnetic nanoparticles can be reconstructed. Furthermore, by solving the linear inversion procedure, the image of the target area containing the magnetic nanoparticles can be reconstructed from the scattered electric field.

S7, calculating the visibility functions of any two receiving and transmitting sensors by calculating scattered magnetic field signals acquired by any two receiving and transmitting sensors on the same plane; specifically, the scattered magnetic field information, detected by any two sensors, of magnetic nanoparticles in the to-be-detected area containing the magnetic nanoparticles can be extracted, and the differences of the scattered magnetic field information detected by the two sensors are compared to obtain the visibility function:

$$\Delta\vec{H}_{scat}(\vec{r_i},\vec{r_j}) = \langle \vec{H}_{scat}(\vec{r_i})\cdot\vec{H}_{scat}(\vec{r_j})\rangle \quad (16)$$

S8, extracting the magnetization information and the scattered electric field information of the magnetic nanoparticles in the to-be-detected area detected by all the sensors and comparing information differences detected by any two sensors one by one to obtain the sum of visibility functions, including phase delay and/or amplitude difference information, namely the total visibility function:

$$Y = \Sigma_i^N \Delta\vec{H}_{scat}(\vec{r_i},\vec{r_j}), i=1,\ldots,N; N\geq 3, a\neq b \quad (17)$$

S9, according to one preferred embodiment, describing the nonlinear observation model for defining the visibility intensity of the target object as follows:

(18)

$$I(\vec{s}) = \left(\frac{j\omega\mu_0}{4\pi}\right)^2 |\sigma(\vec{s}) + j\omega\varepsilon_0\varepsilon_r|^2 \overrightarrow{H_T}(\vec{s})\cdot\overrightarrow{H_T}(\vec{s}') \quad (7)$$

the nonlinear observation model comprises the internal field effect model and the external field effect model; the internal magnetic field induction model is described as follows:

(19)

$$\overrightarrow{H_T}(\vec{r}') = H_{inc}(\vec{r}') - \frac{j}{4\pi\omega\mu_0}\int_V \left[(\overrightarrow{J_m}\cdot\nabla)\nabla + k_0^2\overrightarrow{J_m} + j\omega\mu\times\nabla\right]G(\vec{r},\vec{r}')dV \quad (7)$$

the external magnetic field induction model is described as follows:

$$\vec{H}_{scat}(\vec{r_0}) = \frac{k_0^2}{4\pi} \int_V \left[ (a\vec{H} + b(\vec{H} \cdot \hat{r})\hat{r} \right] G(\vec{r}, \vec{r_0}) dV \quad (7)$$

(20)

S10, according to one preferred embodiment, constructing the two-dimensional image of the target object through an inverse Fourier transform processing mode based on the amplitude and the phase of the dielectric property and the conductivity distribution and the magnetic susceptibility intensity information of the internal tissue, specifically carrying out two-dimensional inverse Fourier transform on visibility function signals acquired by any two sensors to obtain a two-dimensional reconstructed image of the target object:

$$\tilde{I} = \iint Y(\vec{r_i}, \vec{r_j}) e^{-j2\pi(u_{ij}l + v_{ij}m)} du dv \quad (21)$$

The method and the system can be applied to the fields of nondestructive testing, medical imaging, target detection and the like.

Compared with an existing magnetic induction imaging technology, the method and the system have the advantages that the model robustness is high, the imaging quality at the molecular level can be achieved, high-quality rapid recognition of tumor cells can be achieved, and the method based on the magnetic nanoparticles are applied to the concrete issue which is holographic magnetic induction detection of the tumor cells so that the sensitivity and the diagnosis rate of tumor detection are effectively improved, and high-quality holographic magnetic induction imaging for brain imaging at the molecular level is realized for detecting brain tumors.

For example, the term "module" used herein describes any hardware or software, or combination of software and hardware, and is capable of performing the functions associated with the "module".

It should be noted that the specific embodiments are exemplary, and those skilled in the art may envision various solutions within the purview of the disclosure, which are also within the scope of the disclosure and are within the scope of the disclosure. It will be apparent to those skilled in the art that the specification and drawings thereof are illustrative and do not constitute a limitation on the claims. The scope of protection of the disclosure is defined by the claims and equivalents thereof.

It is understandable that same or similar parts in the embodiments can be referred to each other, the unspecified content in some embodiments can refer to the same or similar content in other embodiments.

It is noted that, in the description of the disclosure, the terms such as "first" and "second" are just used for description purpose, but cannot be understood to indicate or hint relative importance. Moreover, in the description of the disclosure, except as otherwise noted, the meaning of "a plurality of" indicates at least two.

Any process, method or block in the flowchart or described in other manners herein may be understood as being indicative of including one or more modules, segments or parts for realizing the codes of executable instructions of the steps in specific logic functions or processes, and that the scope of the preferred embodiments of the disclosure include other implementations, wherein the functions may be executed in manners different from those shown or discussed (e.g., according to the related functions in a substantially simultaneous manner or reverse order), which shall be understood by those skilled in the art.

It should be understood that each component of the disclosure can be realized by using hardware, software, firmware, or the combination of hardware, software, and firmware. In the embodiment, a plurality of steps or methods can be realized by using software or firmware which is stored in a storage device and is executed by an appropriate command executing system. For example, if the steps or methods are realized by using hardware, the steps or methods are the same in another embodiment and can be realized by using any one of the following technologies known in the field or the combination: a discrete logic circuit with a logic gate circuit for realizing a logic function for a data signal, a special integrated circuit with an appropriate combined logic gate circuit, a programmable gate array (PGA), a field-programmable gate array (FPGA) and the like.

Those skilled in the art will appreciate that all or part of the steps carried by a method of implementing the embodiments described above may be accomplished by instructions on associated hardware through a program that may be stored in a computer-readable storage medium that, when executed, includes one or a combination of the steps of an embodiment of the method.

Moreover, each functional unit in each embodiment of the disclosure can be integrated in one processing module, or each unit can exist independently and physically, or two or more units can be integrated into one module. The integrated modules can be achieved in a hardware mode and can also be achieved in a software function module mode. The integrated module can also be stored in a computer-readable storage medium if implemented in the form of a software functional module and sold or used as a stand-alone product.

The above-mentioned storage medium may be a read-only memory, a magnetic or optical disk, or the like.

In the description of the specification, the description of the reference terms such as "one embodiment", "some embodiments", "example", "specific example" or "some examples" indicates to be contained in at least one embodiment or example of the disclosure in combination with specific characteristics, structures, materials or characteristics described by the embodiment or example. In the specification, the schematic expression for the above terms possibly indicates the same embodiment or example. Moreover, the described specific features, structures, materials, or characteristics can be combined in any of one or more embodiments or examples appropriately.

Although the embodiment of the disclosure has already been illustrated and described, it is understood that the embodiment is exemplary but cannot be understood as a limitation of the disclosure, and the embodiment can be changed, amended, replaced, and converted by those skilled in the art in the scope of the disclosure.

What is claimed is:

1. A magnetic induction molecular imaging system for biological tissue detection, characterized by comprising a detection bed, a magnetic nanoparticle device, a magnetic field generating device, a signal receiving and transmitting device, a magnetic field signal acquisition device, and computer equipment, wherein the detection bed is used for bearing the weight of a to-be-detected organism; the magnetic nanoparticle device comprises a release device, the release device is filled with magnetic nanoparticles, and when the to-be-detected organism is measured, the release device sends the magnetic nanoparticles to a to-be-detected area of the detection bed; the magnetic field generating device comprises an electromagnetic wave generating module and Helmholtz coil modules, the electromagnetic wave generating module is used for generating and transmitting electromagnetic waves to the signal receiving and transmitting device, and the Helmholtz coil modules are used for generating an excitation magnetic field for the to-be-detected area; the signal receiving and transmitting device comprises a scanner comprising N sensor arrays, N is a natural number, and sensors are used for receiving the electromagnetic waves transmitted by the magnetic field generating device; the magnetic field signal acquisition device comprises a data acquisition card, and the data acquisition card is used for acquiring scattered electric field information and scattered magnetic field information, based on the magnetic nanoparticles, of the to-be-detected area detected by each sensor on the sensor arrays and sending the scattered electric field information and the scattered magnetic field information to the computer equipment; and the computer equipment is used for analyzing the internal tissue structure state of the to-be-detected organ according to the scattered electric field information and the scattered magnetic field information to form an image.

2. The system according to claim 1, characterized in that the release device is a fiber tube, the upper end and the lower end of the fiber tube are fixed through a support positioning device, and the support positioning device comprises a positioning shell fixedly connected with the end of the fiber tube.

3. The system according to claim 1, characterized in that the number of the Helmholtz coil modules is two, and the two Helmholtz coil modules are respectively arranged at two ends of the sensor arrays.

4. The system according to claim 1, characterized in that the sensor arrays are implemented by columnar sensor arrays, and all sensors are uniformly distributed in a circular ring shape around a target area by taking the axis of the detection bed as the center and are positioned at the same height.

5. The system according to claim 1, characterized in that the magnetic nanoparticles are ferroferric oxide.

6. A magnetic induction molecular imaging method for biological tissue detection realized based on the system according to claim 1, characterized by comprising the following steps: S1, enabling the to-be-detected organism to lie on the detection bed, and exposing the to-be-detected organ in the to-be-detected area; S2, sending quantitative magnetic nanoparticles to the to-be-detected area according to preset settings by the magnetic nanoparticle device; S3, emitting uninterrupted time-harmonic electromagnetic wave signals with a specific frequency and transmitting the signals to the sensor arrays of the signal receiving and transmitting device by the magnetic field generating device, and adjusting the scanning positions of the Helmholtz coils so that the Helmholtz coils generate the excitation magnetic field for the to-be-detected area of the detection bed; S4, detecting the time-harmonic electromagnetic wave signals of the to-be-detected area of the detection bed by the sensor arrays of the signal receiving and transmitting device; S5, acquiring the scattered electric field information and the scattered magnetic field information, based on the magnetic nanoparticles, of the to-be-detected area detected by each sensor on the sensor arrays through the data acquisition card by the magnetic field signal acquisition device; and S6, analyzing the internal tissue structure state of the to-be-detected organ according to the scattered electric field information and the scattered magnetic field information by the computer equipment to form the image.

7. The method according to claim 6, characterized in that the step of analyzing the internal tissue structure state of the to-be-detected organ according to the scattered electric field information and the scattered magnetic field information by the computer to form the image comprises the step of constructing is two-dimensional image of a target object through an inverse Fourier transform processing mode based on the amplitude and the phase of the dielectric property and the conductivity distribution of biological tissue and the magnetic susceptibility intensity information of the internal tissue by the computer.

8. The method according to claim 7, characterized in that the step of constructing the two-dimensional image of the target object through an inverse Fourier transform processing mode based on the amplitude and the phase of the dielectric property and the conductivity distribution of the biological tissue and the magnetic susceptibility intensity information of the internal tissue by the computer comprises the step of carrying out two-dimensional inverse Fourier transform on visibility function signals acquired by any two sensors to obtain a two-dimensional reconstructed image of the target object.

9. The method according to claim 8, characterized in that the acquisition process of a visibility function comprises the following steps: extracting scattered magnetic field information of the magnetic nanoparticles in the to-be-detected area containing the magnetic nanoparticles detected by any two sensors; and comparing differences of the scattered magnetic field information detected by the two sensors to obtain the visibility function of the two sensors.

10. The method according to claim 8, characterized in that the acquisition process of the visibility function further comprises the following steps: extracting the magnetization information and the scattered electric field information, detected by all the sensors, of the magnetic nanoparticles in the to-be-detected area; and comparing information differences detected by any two sensors one by one to obtain the sum of visibility functions, including phase delay and/or amplitude difference information, namely a total visibility function.

* * * * *